(12) United States Patent
Bengtsson et al.

(10) Patent No.: US 10,137,237 B2
(45) Date of Patent: Nov. 27, 2018

(54) NEEDLE ARRANGEMENT

(71) Applicant: Novo Nordisk A/S, Bagsvaerd (DK)

(72) Inventors: Henrik Bengtsson, Taastrup (DK); Lars Eilertsen, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 22 days.

(21) Appl. No.: 15/300,589

(22) PCT Filed: Mar. 25, 2015

(86) PCT No.: PCT/EP2015/056352
§ 371 (c)(1),
(2) Date: Sep. 29, 2016

(87) PCT Pub. No.: WO2015/150179
PCT Pub. Date: Oct. 8, 2015

(65) Prior Publication Data
US 2017/0106135 A1    Apr. 20, 2017

(30) Foreign Application Priority Data
Apr. 3, 2014  (EP) .................................... 14163426

(51) Int. Cl.
*A61M 5/00* (2006.01)
*A61M 5/34* (2006.01)
*A61M 5/32* (2006.01)

(52) U.S. Cl.
CPC ............ *A61M 5/001* (2013.01); *A61M 5/326* (2013.01); *A61M 5/347* (2013.01); *A61M 5/3297* (2013.01); *A61M 2005/3267* (2013.01)

(58) Field of Classification Search
CPC ...... A61M 5/001; A61M 5/326; A61M 5/347; A61M 2005/3257; A61M 2005/3267; A61M 5/3297
See application file for complete search history.

(56) References Cited

U.S. PATENT DOCUMENTS 4,416,663 A * 11/1983 Hall ...................... A61M 5/326
604/198
4,507,118 A    3/1985 Dent
(Continued)

FOREIGN PATENT DOCUMENTS

WO       03/045480      7/2003
WO     2008/077706 A1   7/2008
(Continued)

*Primary Examiner* — Lauren P Farrar
(74) *Attorney, Agent, or Firm* — Wesley Nicolas (57) ABSTRACT

The present invention relates to a needle arrangement for an injection device. The needle arrangement is made up from needle cannula which is mounted such that a distal part having a distal tip extends in a distal direction. Further, a telescopically movable shield carrying a cleaning chamber surrounds at least the tip of the needle cannula between injections such that the tip of the needle cannula is maintained inside the cleaning chamber between subsequent injections. The cleaning chamber is at least distally provided with a pierceable septum through which the needle cannula penetrates during injections. For guiding the needle cannula during injections a telescopically movable tube is provided. During injections the distal end of the telescopically movable tube at least partly penetrates the distal septum.

12 Claims, 5 Drawing Sheets

(56) References Cited

U.S. PATENT DOCUMENTS

| | | | |
|---|---|---|---|
| 4,634,424 | A | 1/1987 | O'Boyle |
| 4,666,436 | A | 5/1987 | McDonald et al. |
| 2003/0014018 | A1 | 1/2003 | Giambattista et al. |
| 2003/0060776 | A1 | 3/2003 | Heiniger |
| 2008/0177237 | A1 | 7/2008 | Stonehouse et al. |
| 2011/0257603 | A1 | 10/2011 | Ruan et al. |
| 2011/0288491 | A1* | 11/2011 | Newman .............. A61M 5/326 604/198 |

FOREIGN PATENT DOCUMENTS

| | | |
|---|---|---|
| WO | 2014029018 A1 | 2/2014 |
| WO | 2014064100 A1 | 5/2014 |
| WO | 2015062845 A1 | 5/2015 |

* cited by examiner

NEEDLE ARRANGEMENT

CROSS-REFERENCE TO RELATED APPLICATIONS

This application is a 35 U.S.C. § 371 National Stage application of International Application PCT/EP2015/056352 (published as WO 2015/150179), filed Mar. 25, 2015, which claims priority to European Patent Application 14163426.1, filed Apr. 3, 2014; the contents of which are incorporated herein by reference.

THE TECHNICAL FIELD OF THE INVENTION

The invention relates to a needle arrangement in which a shielded needle cannula is mounted such that a distal part extends in a distal direction. The needle cannula is preferably secured in a hub which is either detachable or permanently secured to an injection device. The invention especially relates a needle arrangement having a needle cannula for multiple use and which needle cannula is cleaned between subsequent injections.

DESCRIPTION OF RELATED ART

Shielded needle assemblies are widely known. WO 2003/045480 discloses a safety needle assembly in which the axially movable shield locks after one injection such that the needle assembly cannot be reused.

WO 2008/077706 discloses a similar construction wherein the telescopic shield is prevented from axial movement when the needle assembly is removed from the injection device. However, every time the needle assembly is mounted onto the injection device the shield is unlocked to move axially.

Injection devices wherein the tip of the needle cannula is maintained in a cleaning solvent between subsequent injections are disclosed in U.S. Pat. No. 4,416,663, U.S. Pat. No. 4,507,118 and in U.S. Pat. No. 4,666,436. As can be seen from these prior art injection devices, the cleaning chamber is usually carried distally on a retractable shield covering the tip of the needle cannula between subsequent injections.

Further, WO2014/064100 discloses a pre-filled disposable injection device which has a telescopically shield covering the tip of the needle cannula between subsequent injections. This telescopically shield is urged into a distal covering position by a spring. Further, in one embodiment, the shield is provided with a hollow chamber containing a liquid solvent such as a chemical disinfectant or biocide which cleans the tip of the needle cannula between subsequent injections.

Examples on such cleaning solvents are provided in WO 2014/029018. However, as disclosed in PCT/EP2014/071746 it is sometime preferred to use the preservative contained in the drug as the cleaning solvent. This is preferably done by filling the cleaning chamber with liquid drug directly from the cartridge embedded in the pre-filled injection device and thus use a quantum of the liquid drug as the cleaning solvent.

Needle cannulae being used for injection of insulin and similar liquid products for the treatment of diabetes are usually very thin. Needle cannulae as thin as Gauge 33 which is defined by an outside diameter of only one fifth of a millimeter are manufactured and sold today. The sharp distal tip of these known needle cannulae is usually produced by grinding or electro polishing or a combination thereof.

If needle cannulae having such small diameter are to be used for multiple injections it is very important to protect the needle cannula against physical damages. In a set-up in which the distal tip of the needle cannula many times have to penetrate through a septum, the sharpness of the needle cannula will eventually wear out which increases the pain of administering the injection.

DESCRIPTION OF THE INVENTION

It is henceforth an object of the present invention to provide a needle arrangement wherein the thin needle cannula is protected against physical damages both before injection, during injection and after injection. It is especially an object to provide a needle arrangement in which the physical wear on the distal tip of the needle cannula is reduced.

The invention is defined in the attached claim 1 followed by a number of embodiments. The individual claims are explained in details in the following.

Accordingly, in one aspect of the present invention, the needle arrangement comprises:

- A needle cannula with a lumen and mounted such that a distal part having a distal tip extend in a distal direction,
- A telescopically shield slidable between a first extended position and a second retracted position. The telescopically shield carries distally a cleaning chamber containing a cleaning solvent for cleaning at least the tip of the needle cannula between subsequent injections and which cleaning chamber at least distally is provided with a pierceable distal septum. The first extended position being a position in which the shield is extended to cover at least the tip of the needle cannula and the second position being a position in which the shield is retracted to a position exposing at least the tip of the needle cannula to perform an injection.
- A telescopically movable tube for guiding the needle cannula, the telescopically movable tube having a tube lumen and a distal end wherein the needle cannula is guided inside the tube lumen and wherein the distal end of the telescopically movable tube at least partly penetrates the distal septum when the telescopically shield is moved from the first extended position to the second retracted position.

The needle cannula or at least the distal part thereof is guided inside the tube lumen and since the telescopically movable tube does the actual penetration of at least the distal septum of the cleaning chamber, the distal tip of the needle cannula is not exposed to the wear of simultaneously penetrating the septum as the penetration is done by the telescopically movable needle cannula. As a result of both the guiding and the reduced exposing of the distal tip of the needle cannula, a very thin needle cannula can be used many times without the sharpness of the tip wearing out.

In one example the distal tip of the telescopically movable tube only penetrates into the proximal part of the distal septum and not all the way through the distal septum. This provides for a faster and better self-sealing of the septum material. However, it does expose the distal tip of the needle cannula to some wear.

In another example, the telescopically movable tube penetrates all the way through the distal septum which prevents the distal tip of the needle cannula from physically touching the outer membrane which increases the life time of the needle cannula. Further, since the distal tip of the needle cannula is not in physical contact with the distal septum of the cleaning chamber it also prevents the distal tip of the needle cannula from being contaminated should dirt be collected on the distal and outer surface of the distal septum.

The needle cannula is preferably mounted such that the needle arrangement makes up a pen-needle with the distal part extending in a distal direction and the proximal part of the needle cannula extending in a proximal direction.

The needle cannula can either be mounted in a hub together making up a needle assembly which is attachable to the injection device or the needle cannula can be mounted on the injection device without the possibility of being removed. When permanently mounted on the injection device the needle cannula can either be mounted directly on the housing of the injection device without a needle hub or it can be mounted in a needle hub which is then permanently secured to the injection device.

Further, the telescopically movable tube is permanently secured to a tube hub. The telescopically movable tube can be made from a metallic material and connected to the hub e.g. by gluing or moulding. The tube hub is preferably moulded from a suitable polymeric material. In one embodiment, the telescopically movable tube and the tube hub is both moulded from a suitable polymer and preferably moulded as one unitary unit.

No matter how the telescopically movable tube and the tube hub are attached, the tube hub is movable mounted relatively to the needle hub such that both the tube hub and thus the telescopically movable tube can telescope axially in relation to the needle hub.

Further, a first spring urges the tube hub in a distal direction. The first spring is preferably provided between the needle hub and the tube hub.

A second spring is arranged to urge the telescopically shield into the first extended position covering the tip of the needle cannula. This second spring is preferably mounted between the shield and the needle hub.

When not in use, the shield covers both the telescopically movable tube and the distal tip of the needle cannula. During injection, however, the shield would be forced in a proximal direction as it is pressed against the skin of the user. This would expose first the telescopically movable tube and consequently the distal tip of the needle cannula.

However, in one embodiment the geometry can be such that the telescopically movable tube does not fully penetrate through the distal septum.

The cleaning chamber can be formed as a separate unit carried by the shield or it can be produced as an integral part of the shield e.g. as a room which is distally sealed by the distal septum and proximally by a proximal septum. Both the distal septum and the proximal septum are preferably made from the same rubber material usually used for forming the septum of cartridges.

The needle assembly herein described can either be made as a separate needle assembly connectable to an injection device or the needle arrangement can be made integral with the injection device.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula supposed to be inserted into the skin of the user whereas the term "proximal end" is meant to refer to the opposite end pointing away from the user during injection.

Further, as indicated in the figures, the axis "X" is the longitudinal axis of the injection device and thus defines the axial direction of the injection device.

The invention is disclosed in the FIGS. 1 to 6 which discloses a needle assembly 1 attached to a pen-shaped injection device 2. The pen-shaped injection device 2 secures a cartridge 5 containing the liquid drug to be injected.

The needle assembly 1 comprises a needle hub 10 carrying a needle cannula 20. The needle cannula 20 is preferably glued to the needle hub 10 but could be mounted in a number of alternative ways e.g. by welding.

Figure 1:
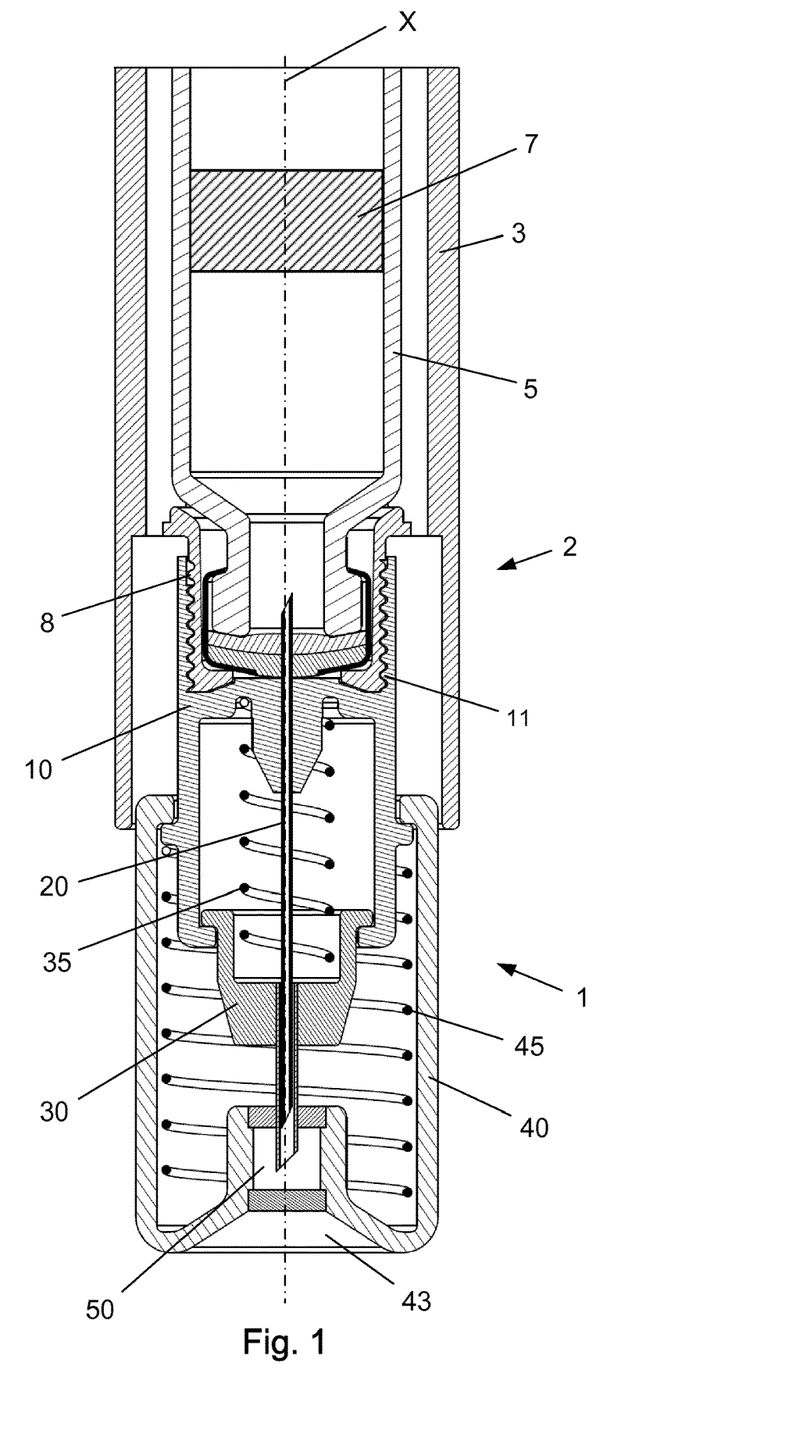
FIG. 1 shows a cross sectional view of the needle arrangement according to the invention prior to performing an injection i.e. with the telescopically shield in the first extended position.

Further, FIG. 1 discloses a tube hub 30 which is urged in a distal direction by a first spring 35 and a telescopic slidable shield 40 covering the tube hub 30 and urged in distal direction by a second spring 45.

The telescopically movable shield 40 is distally provided with a cleaning chamber or reservoir 50 which is filled with a cleaning solvent cleaning the needle cannula 20 between injections. The cleaning solvent is preferably identical to the drug contained in the cartridge 5 such that the cleaning chamber 50 is filled with drug directly from the cartridge 5 before initiating the first injection.

The housing 3 of the injection device 2 secures the cartridge 5 which comprises an interior containing the liquid drug to be injected. The interior is distally sealed by a septum 6 and proximally by a movable plunger 7. The plunger 7 is preferably moved forward by a non-shown piston rod driven by a drive mechanism.

In the disclosed embodiment, the injection device 1 is provided with a thread 8 securing the needle assembly 1 which is attached via a thread 11 provided on the needle hub 10. However, the needle assembly 1 can be mounted in numerous ways.

Further, the needle assembly 1 could be an integral part of the injection device 2 such that it cannot be removed. This is particular useful if the injection device is meant to be a pre-filled injection device carrying a needle cannula to be used for several injections.

In one embodiment, the needle hub 10 to which the needle cannula 20 is secured could be made integral with the injection device or permanently attached to the injection device to form one single unit.

Figure 2:
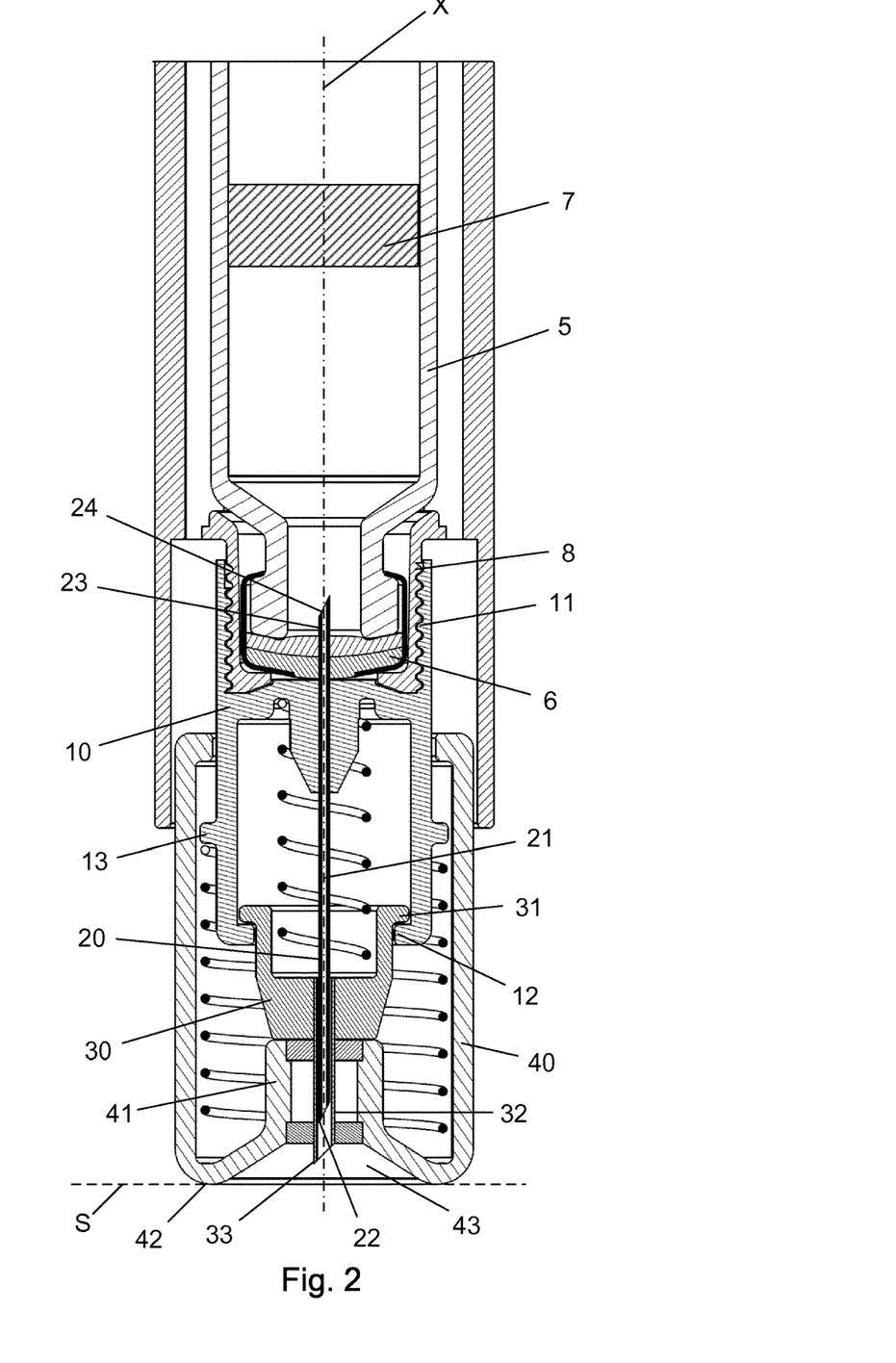
FIG. 2 shows a cross sectional view of the needle arrangement with the telescopically movable tube fully penetrated through the distal septum and the telescopically shield partly in the second retracted position.

As indicated in FIG. 2, the needle assembly is in the form of a pen-needle. The needle cannula 20 comprises a distal part 21 having a distal tip 22 for penetrating the skin of the user (depicted as "S" in the FIGS. 5 and 6) and a proximal end 23 for penetrating into the injection device 2 to which the needle assembly 1 is connected. The needle cannula 20 further has a longitudinal lumen 24 stretching along the centre line "X".

When the plunger 7 is moved forward, the volume of the interior of the cartridge 5 decreases and the liquid drug is pressed out through the lumen 24 of the needle cannula 20 having its proximal part 23 penetrated through the septum 6 and into the interior of the cartridge 5.

Distally the needle hub 10 is provided with an inwardly pointing flange 12 which supports a tube hub 30 having an outwardly pointing flange 31 at its proximal end. The tube hub 30 is urged distally and pressed against the inwardly pointing flange 12 by a spring 35 encompassed between the needle hub 10 and the tube hub 30. The tube hub 30 is thus able to move axially in relation to the needle hub 10. A groove and tongue engagement can be provided to prevent relative rotation of the tube hub 30.

The telescopically shield 40 is slidable mounted on the external surface of the needle hub 10 and urged in a distal direction be the second spring 45 encompassed between the needle hub 10 and the telescopically shield 40. Proximally this second spring 45 preferably rests on an outwardly flange 13 provided peripherally on the needle hub 10.

Figures 3, 4:
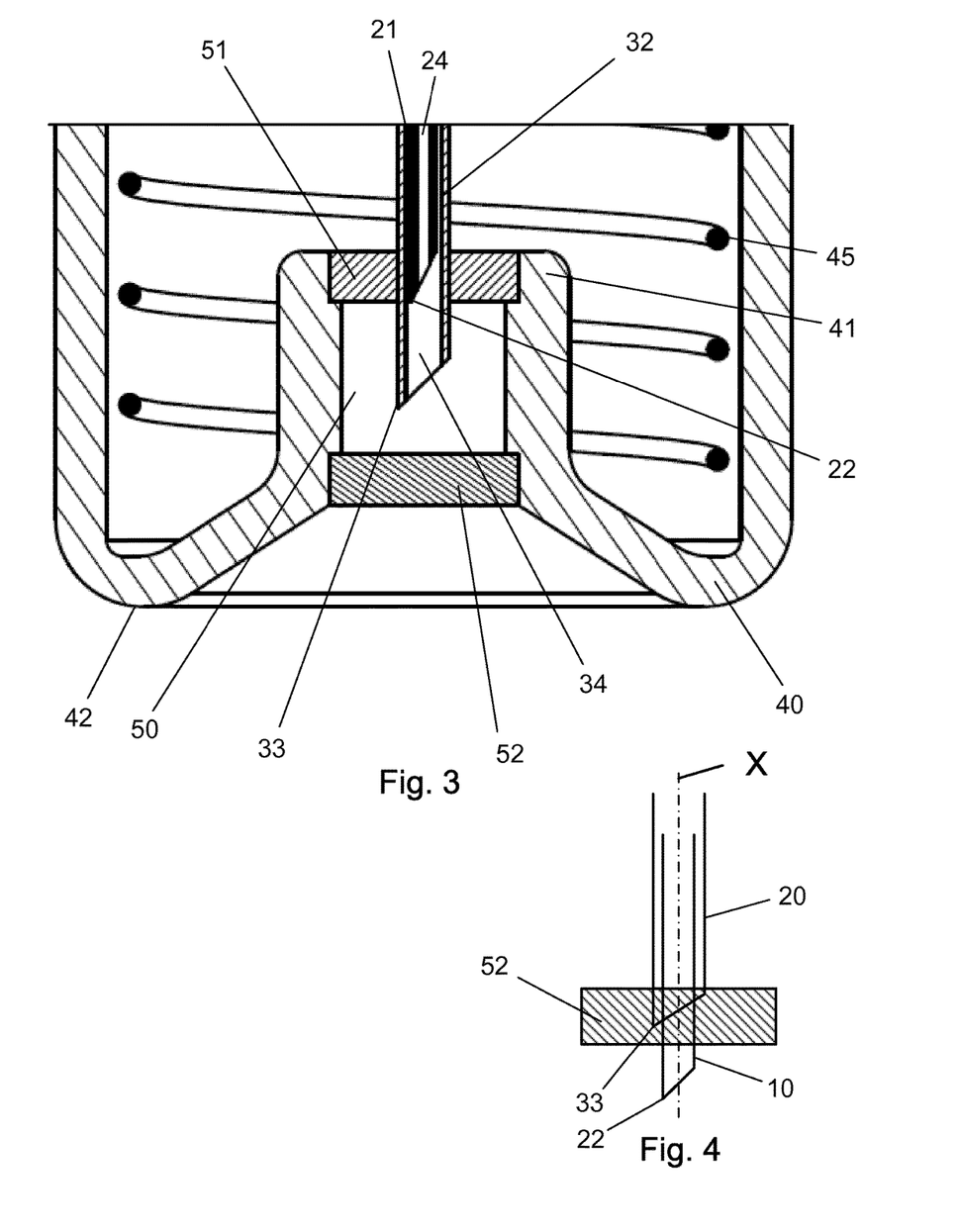
FIG. 3 shows a close-up view of the distal tip of the needle arrangement in the position depicted in FIG. 1.
FIG. 4 shows a schematic view of the telescopically movable tube only partly inserted into the distal septum.

Distally the tube hub 30 carries a telescopically movable tube 32 which is depicted in an enlarged form in FIG. 3. The telescopically movable tube 32 has a pointed tip 33 and a lumen 34 and is preferably permanently secured to the tube hub 30 such that the telescopically movable tube 32 moves axially together with the tube hub 30. The tube hub 30 and the telescopically movable tube 32 can in one example be moulded as one unitary unit, preferably from a suitable polymeric material. However, the telescopically movable tube 32 can also be provided as a metallic part secured to a polymeric tube hub 30.

The needle cannula 20 and preferably the proximal part 21 of the needle cannula 20 slide inside the lumen 34 of the telescopically movable tube 32. In order to guide the needle cannula 20 properly, the outside diameter of the needle cannula 20 need to be only a little less than the inside diameter of the telescopically movable tube 32.

Further, the tip 33 of the telescopically movable tube 32 is located inside the cleaning chamber 50 between injections. The cleaning chamber 50 is formed between a proximal septum 51 and a distal septum 52. The cleaning solvent inside the cleaning chamber 50 is also in contact with the distal tip 22 of needle cannula 20 via the lumen 34 of the telescopically movable tube 32.

Between subsequent injections, the tip 33 of the telescopically movable tube 32 and the distal tip 22 of the needle cannula 20 are maintained submerged in the cleaning solvent in the cleaning chamber 50 as depicted in FIG. 1.

Figure 5:
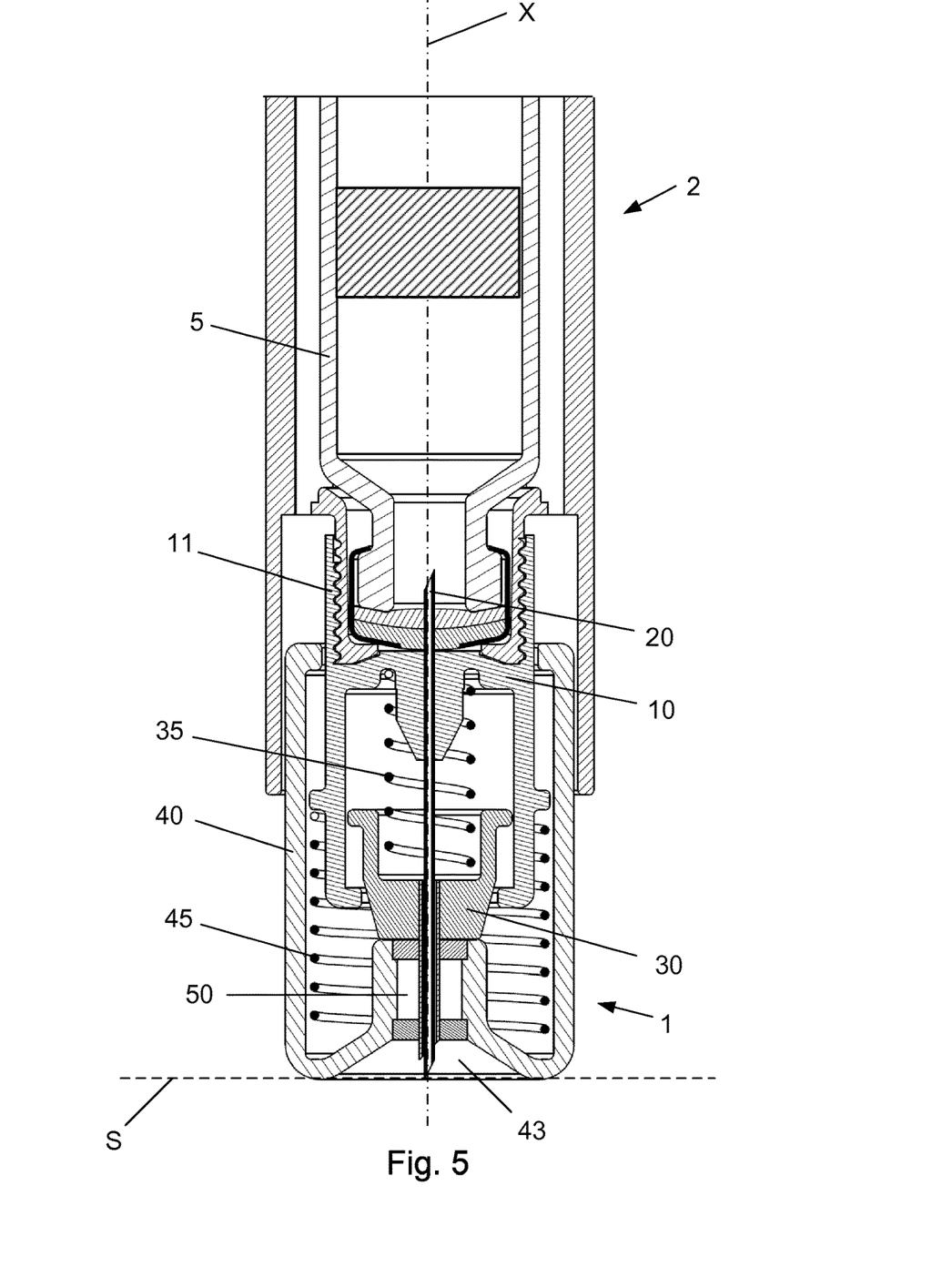
FIG. 5 shows a cross sectional view of the needle arrangement with the distal tip of the needle cannula exposed.

When an injection is performed, the user presses the distal surface 42 of the telescopically shield 40 against the skin S as depicted in FIG. 5. This makes the tip 33 of the telescopically movable tube 32 penetrate through the distal septum 52. At the same time, the tube hub 30 abuts an internal flange 41 on the telescopically shield 40 thereby preventing the telescopically movable tube 32 from penetrating further.

Figure 6:
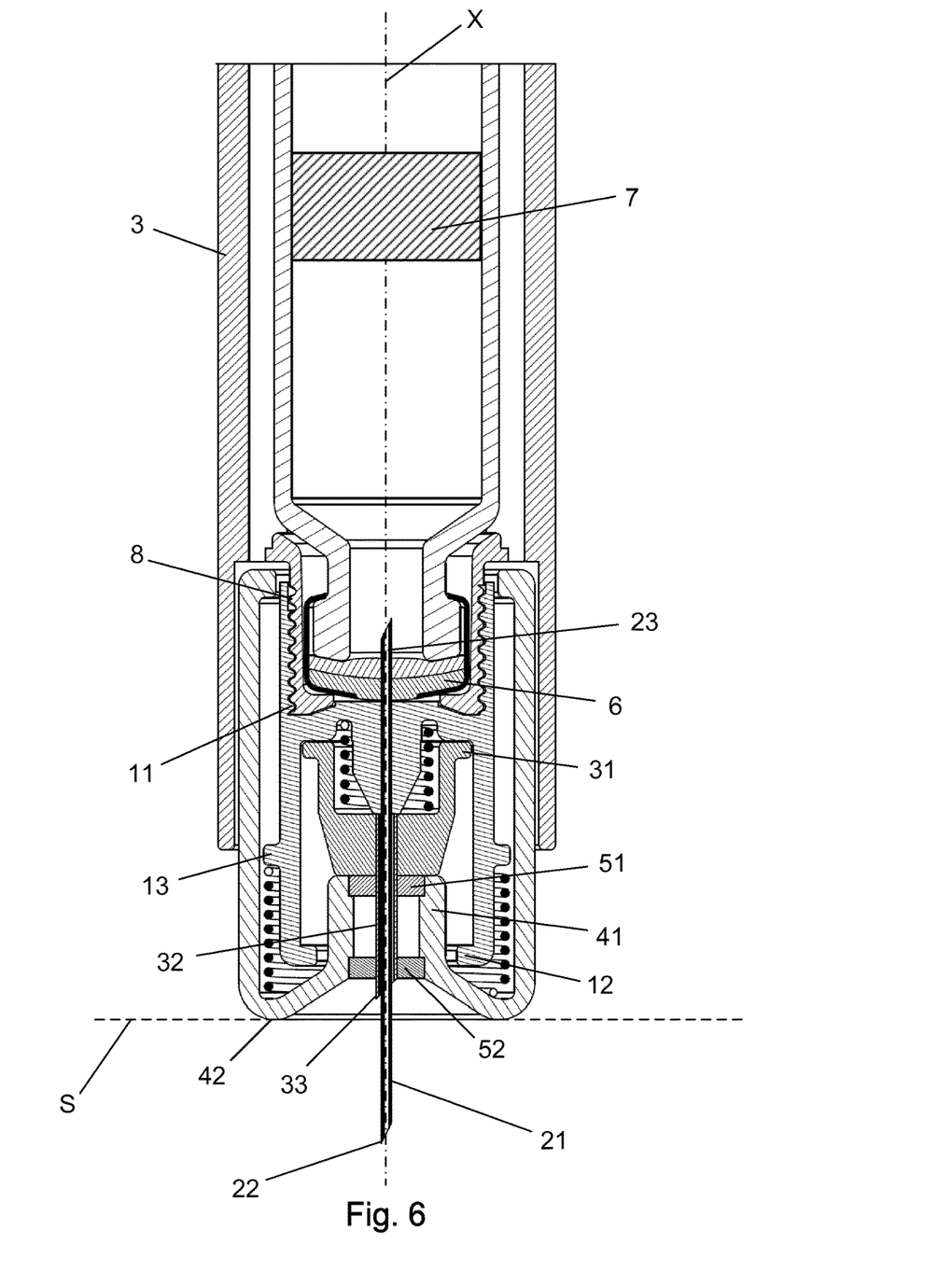
FIG. 6 shows a cross sectional view of the needle arrangement with the needle cannula fully exposed.

As the telescopically shield 40 is moved further in the proximal direction as depicted in FIG. 6, the tube hub 30 is pushed proximally by the telescopically shield 40. This proximal movement of the tube hub 30 and the telescopically movable tube 32 now exposes the distal tip 22 of the needle cannula 20.

As depicted in FIG. 4, the geometry can be such that the tip 33 of the telescopically moveble tube 32 does not penetrate fully through the distal septum 52. The most distal penetration is thus made by the tip 22 of the needle cannula 30 and not by the telescopically movable tube 32. This minimizes the diameter of the temporary opening cut in the distal septum 52 thus making it easier for the inherent resiliency of the septum material to re-seal the opening when the needle cannula 20 retracts to the position disclosed in FIG. 1 after injection.

In FIG. 6, the distal part 21 of the needle cannula 20 is fully inserted into the skin of the user and the injection of the liquid drug is executed either manually or automatically.

The distal surface 42 is preferably provided with a recess 43 into which the proximal septum 52 is sunk. This has the benefit that a space is provided between the surface of the skin "S" and the distal surface of the distal septum 52 during injection such that the pointed tip 33 of the telescopically movable tube 32 can be maintained within this space as the distal tip 22 of needle cannula 20 travels further into the skin "S" as depicted in FIG. 6. However, in the example depicted in FIG. 4, this recess 43 is not needed since the telescopically movable tube 32 does not penetrate fully through the distal septum 52.

After the set dose of liquid drug has flown into the body of the user, the user removes the distal end of the shield 40 from the skin "S" where after the second spring 45 moves the needle shield 40 distally and the first spring 35 moves the tube hub 30 distally. The starting position disclosed in FIG. 1 is thereby obtained and the distal tip 22 of the needle cannula 20 is automatically moved back into the cleaning chamber 50.

Some preferred embodiments have been shown in the foregoing, but it should be stressed that the invention is not limited to these, but may be embodied in other ways within the subject matter defined in the following claims.

The invention claimed is:

1. A needle arrangement for an injection device comprising:
   a needle cannula having a lumen and mounted such that a distal part having a distal tip extend in a distal direction,
   a telescopically movable shield slidable between a first extended position and a second retracted position and wherein the telescopically movable shield distally carries a cleaning chamber containing a cleaning solvent for cleaning at least the tip of the needle cannula between subsequent injections and which cleaning chamber at least distally is provided with a pierceable distal septum, wherein the telescopically movable shield in the first extended position is extended to at least cover the distal tip of the needle cannula and in the second retracted position is retracted to at least expose the tip of the needle cannula,
   a telescopically movable tube for guiding the needle cannula, the telescopically movable tube having a tube lumen and a distal end wherein the needle cannula is guided inside the tube lumen, and which tube lumen is movable relatively to the needle cannula, and wherein the distal end of the telescopically movable tube at least partly penetrates the distal septum when the telescopically movable shield is moved from the first extended position to the second retracted position.

2. A needle arrangement according to claim 1, wherein the needle cannula is mounted such that the distal part extends in a distal direction and a proximal part extend in a proximal direction.

3. A needle arrangement according to claim 1, wherein the needle cannula is mounted in a needle hub thus making up a needle assembly.

4. A needle arrangement according to claim 3, wherein the needle hub is provided with fastening means for securing the needle assembly to an injection device.

5. A needle arrangement according to claim 1, wherein the telescopically movable tube is secured to a tube hub.

6. A needle arrangement according to claim 5, wherein the tube hub is movable mounted relatively to the needle hub.

7. A needle arrangement according to claim 6, wherein a first spring urges the tube hub in a distal direction.

8. A needle arrangement according to claim 7, wherein the telescopically movable shield is urged into the first extended position by a second spring.

9. A needle arrangement according to claim 1, wherein the cleaning chamber is defined by a proximal septum and the distal septum.

10. A needle arrangement according to claim 9, wherein the proximal septum and the distal septum are attached to the telescopically movable shield.

11. An injection device having a needle arrangement according to claim 1 attached thereto.

12. An injection device according to claim 11, wherein the needle arrangement is permanently attached thereto.

* * * * *